United States Patent
Bader et al.

(10) Patent No.: US 9,480,612 B2
(45) Date of Patent: Nov. 1, 2016

(54) COMPOSITE WEB

(71) Applicant: MONDI CONSUMER PACKAGING TECHNOLOGIES GMBH, Gronau (DE)

(72) Inventors: Herbert Bader, Nordwalde (DE); Marcel Grossmann, Essen (DE)

(73) Assignee: Mondi Consumer Packaging Technologies GmbH, Gronau (DE)

( * ) Notice: Subject to any disclaimer, the term of this patent is extended or adjusted under 35 U.S.C. 154(b) by 72 days.

(21) Appl. No.: 14/666,521

(22) Filed: Mar. 24, 2015

(65) Prior Publication Data

US 2016/0279000 A1    Sep. 29, 2016

(51) Int. Cl.
*A44B 18/00* (2006.01)
*A61F 13/62* (2006.01)
*A61F 13/56* (2006.01)

(52) U.S. Cl.
CPC ......... *A61F 13/625* (2013.01); *A61F 13/5622* (2013.01)

(58) Field of Classification Search
CPC ................ Y10T 428/24017; A61F 13/49015; B32B 37/20
USPC .......................................................... 428/100
See application file for complete search history.

(56) References Cited

U.S. PATENT DOCUMENTS

| | | | |
|---|---|---|---|
| 5,846,262 A | 12/1998 | Sayama et al. | |
| 7,422,991 B2 | 9/2008 | Baldauf et al. | |
| 7,704,901 B2 | 4/2010 | Baldauf et al. | |
| 8,337,651 B2 | 12/2012 | Schoenbeck | |
| 8,496,773 B2 | 7/2013 | Bader et al. | |

FOREIGN PATENT DOCUMENTS

| | | |
|---|---|---|
| EP | 0768075 | 4/1997 |
| EP | 1736306 | 12/2006 |
| EP | 2301502 | 3/2011 |
| EP | 2340796 | 7/2011 |
| WO | WO 99/13745 | 3/1999 |

*Primary Examiner* — Alexander Thomas
(74) *Attorney, Agent, or Firm* — Michael J. Striker (57) ABSTRACT

A composite web, with elastic and inelastic regions, is formed to separated or punched into diaper closure elements. The composite web includes nonwoven web which forms a first outer side of the composite web. On the composite web are disposed spaced-apart, elastically stretchable foil strips. A nonwoven material covers the elastically stretchable foil strips on a second outer side of the composite web. At least one inelastic strip of a hook material bridges a region between two adjacent, elastically stretchable foil strips. The nonwoven material overlaps edges of the strip of hook material. The strip of hook material has projections on the edges thereof that are overlapped by the nonwoven material. The projections extend into the nonwoven material.

10 Claims, 9 Drawing Sheets

COMPOSITE WEB

BACKGROUND OF THE INVENTION

The present invention relates to composite web having elastic and inelastic regions, from which diaper closure elements can be separated or punched. The composite web comprises a nonwoven web forming a first outer side; spaced-apart, elastically stretchable strips that are disposed on the nonwoven web; a nonwoven material that covers the elastically stretchable strips on a second outer side; and at least one inelastic strip of a hook material, which bridges a region between two adjacent, elastically stretchable strips.

In the production of composite webs for diaper closure elements, it is known from EP 2 301 502 A1 to laminate elastic strips between two flat nonwoven webs, wherein a direct connection of the two nonwoven webs and the incorporation of a reinforcing strip occur in alternation between two adjacent, elastically stretchable foil strips. At the point where the two nonwoven webs are directly interconnected, the diaper closure element can be attached to a disposable article such as a baby diaper or a hygiene product for adults, while the section having the elastically stretchable foil strip imparts the required elasticity to the diaper closure element. A hook strip can be subsequently applied at the point where the reinforcing strip is disposed, wherein the reinforcing strip is required in order to prevent the nonwoven material from tearing in an uncontrolled manner when under tension. For the same reason, an overlap between the reinforcing strip and the elastically stretchable foil strip is also provided.

A composite web having elastic and inelastic regions is also known from EP 1 736 306 A1, according to which elastic and inelastic regions are formed by a corresponding application of adhesive. The adhesive is provided in order to strengthen the material to a sufficient extent, wherein adhesive is provided only in sections on elastically stretchable film strips. The subsequent placement of a hook material on the outer side can be problematic, however, because the material underneath the hook strip is reinforced by only one continuous layer of adhesive.

A composite web having the initially described features is known from EP 2 340 796 A1, wherein the hook material in this case also is glued onto the outside of two flat nonwoven strips. In order to provide the material with sufficient strength overall, a further, inelastic strip is provided for reinforcement on the opposite side. The application of two opposing, inelastic material strips is expensive in terms of material costs and is complicated to carry out.

Document EP 0 768 075 B1 makes known a disposable diaper having reclosure elements on the sides. The reclosure elements do not have elastic regions. The necessary elasticity of the entire disposable diaper is achieved in that an elastic element is disposed in a front waist region, while the diaper closure elements in the form of lateral wings are rigid. A hook material is provided on the lateral diaper closure elements. The hook material is covered on the edges thereof by a protective layer made of a nonwoven material. The protective layer made of a nonwoven material is provided for completely covering the hooks in order to form a soft gripping section for a user.

Document WO 99/13745 A1 makes known a hook material having hook-free edges, wherein the hook-free edges are covered by a cover material. The above-described arrangement is intended to be disposed in the waist region of a diaper in order to permit diaper closure elements comprising a loop material to be attached thereto. The document does not describe designing the arrangement known from WO 99/13745 A1 to be elastic in sections.

SUMMARY OF THE INVENTION

The present invention overcomes the shortcomings of known arts, such as those mentioned above.

To that end, the present invention provides a planning a composite web having elastic and inelastic regions, from which diaper closure elements can be separated or punched. The inventive composite web realizes a particularly reliable fastening of a hook material possible. In addition, a suitable method is provided for the production of such a composite web.

The invention provides that a nonwoven material overlaps edges of a strip of hook material, wherein the strip of hook material has projections on the edges thereof that are overlapped by the nonwoven material, where the projections extend into the nonwoven material.

The invention is advantageous for various reasons, which include but are not limited to the following. First, the hook material is integrated into the composite web in an improved manner via the overlap by the nonwoven material. The edges of the hook material are disposed so as to be covered, and therefore, the edges are not accessible and are well-protected.

The elements of the composite web are typically bonded and/or welded to one another. Since the projections extend into the nonwoven material at the overlapped edges of the strip of hook material, a mechanical connection additionally results. Due to the projections engaging into the nonwoven material, a mechanical connection comprising a form-fit connection results in the plane of the composite web. It is therefore possible to reliably prevent the composite web from tearing at the transition from the elastic region to the inelastic region, even when subjected to very high loads.

An additional reinforcement is always required in the region of the hook material in the case of the composite webs known from the prior art that have elastic and inelastic regions from which diaper closure elements can be punched. According to the present invention, this function is performed by the hook material itself. The hook material is an integral component in the layer structure of the composite web.

In an embodiment, the projections extend through the nonwoven material. The entire thickness of the nonwoven material is then used for mechanical anchoring in the manner of a form-fit connection. The projections extending through the nonwoven material can have heads on the ends thereof, the heads having an angling and/or thickening. A secure fixation of the nonwoven material also is obtained perpendicularly thereto, in addition to a form-fit connection in the plane of the composite web. In other words, the angling and/or thickening of the projections serves to prevent the nonwoven material from being lifted upwardly at the overlapping edges. In addition to a bonding, which is usually provided, the angling and/or thickening of the projections serves also results in a particularly secure and reliable connection.

The hook material comprises a carrier section and exposed hooks between the edges, which are covered by the nonwoven material. The hooks are provided for connection to a suitable loop material. The projections are preferably disposed on the carrier section. For example, the entire hook material can be made of a thermoplastic plastic, wherein the exposed hooks and the projections are then drawn or pressed out of the carrier section in the molten state.

Independently of the exact type of manufacture, the nonwoven material at the overlapped edges preferably rests on the carrier section. In other words, the nonwoven material provided on the second outer side of the composite web is placed directly on the carrier section. As a result, the projections extend far into the nonwoven material, wherein the nonwoven material in the overlapped region also can be bonded on the carrier section. The advantage also results that the nonwoven material at the overlapped edges is as flat as possible and is well-protected.

The exposed hooks between the edges that are covered by the nonwoven material and the projections disposed in the covered regions can have the same shape. The projections and the hooks then differ in that the projections are surrounded by the nonwoven material, while the hooks are exposed. The projections effect an interlocking connection with a loop material.

The heads of the exposed hooks and the projections can be produced in the shape of an angling and/or thickening before or after the individual layers of the composite web are connected. If the projections are provided with heads before the connection with the nonwoven material is established, with the creation of a form-fit connection, the nonwoven web must be guided over these heads, wherein elastically resilient pressure rollers or the like can be used for this purpose.

In an embodiment, however, heads in the form of an angling and/or thickening are not formed until after the individual components of the composite web are joined. An inelastic strip is then provided, which initially only has stems, which extend away from the carrier section. When the nonwoven material is then placed thereon, it easily pierced by the stems at the edges of the inelastic strip. Subsequent thereto, within the scope of the described variant, heads having an angling and/or thickening are then formed on the ends of the stems. The stems then become the exposed hooks between the overlapped edges and become the projections connected to the nonwoven material in a form-fit manner.

The heads are produced, in particular, by the effect of pressure and temperature. It is expedient, therefore, that the stems for forming the projections connected in a form-fit manner are more extremely shaped by use of a suitable embodiment of the tool used for the shaping. It is thereby possible to establish an intimate and reliable connection between the inelastic strip of hook material and the nonwoven material disposed so as to overlap the edges.

The overlapping region between the strip of hook material and the nonwoven material is selected such that a secure fastening is made possible. The region of overlap can be between 2 mm and 30 mm, is preferably between 8 mm and 20 mm and most preferably 12 mm.

The elastically stretchable strips are formed from an elastically stretchable foil. The nonwoven material that covers the elastically stretchable strips or foil strips on the second side of the composite web is formed of nonwoven strips that are spaced apart from one another. The elastically stretchable strips can be guided directly up to the inelastic strips of hook material or terminate at a distance, for example, a few millimeters from the inelastic strip of hook material. The transition region on the second outer side is covered and protected by the nonwoven material that is present there. The nonwoven material therefore extends in the direction of the inelastic strip of hook material beyond the elastically stretchable strip.

In an embodiment, the hook material is attached directly to the flat nonwoven web. The elastically stretchable foil strips are attached directly on the nonwoven web.

Various means for attachment are contemplated by the invention. For example, the attachment may be implemented by use of an adhesive, which is selectively applied over the entire surface or only in regions. Depending on the type of bonding and depending on the materials and the loads, a strip-shaped bonding also can be used for securely attaching the hook material. It must also be considered, in this case, that greater strength is achieved by use of the form-fit connection of the hook material to the nonwoven material on the second outer side.

Due to the strip-shaped bonding, it is possible to save adhesive and thereby reduce costs. It must be considered, in this case, that suitable adhesives are not only relatively expensive, but also can adversely affect elasticity. This negative influence of the adhesive is reduced by a strip-shaped application underneath the elastically stretchable strip. A strip-shaped application of adhesive parallel to the extension of the elastically stretchable strip is advantageous, in particular, wherein the individual diaper closure elements made of the composite web are stretched transversely thereto when used.

The elastically stretchable strips are preferably made of a foil of a suitable thermoplastic elastomer, wherein a polymer from the group comprising styrene-butadiene-styrene block copolymers (SBS), styrene-isoprene-styrene block copolymers (SIS), styrene-ethylene-butylene-styrene block copolymers (SEBS), elastic polyethylene copolymers, elastic polypropylene copolymers, elastic polyurethane copolymers, elastic polyamide copolymers or a mixture of these polymers is suitable. In addition to a use of monofoils, it also is possible to use co-extruded foils, wherein co-extruded foils having a plurality of identical layers also are suitable. Foil strips having a thickness between 10 and 130 μm are particularly suitable.

The nonwoven material covering the elastic strips on the second outer side and the nonwoven web disposed on the opposite side of the composite web are usually not elastic themselves, but are stretchable to such a sufficient extent that these can form the elastic regions of the composite web. The necessary stretchability also can be achieved, however, by activating the composite web by an initial stretching in which the nonwoven layers are also partially destroyed, i.e., torn. The nonwoven material imparts a soft textile feel to the composite web.

The invention includes a method for the production of the described composite web, wherein a nonwoven web, elastically stretchable strips, strips of a nonwoven material and an inelastic strip comprising projections on the edges thereof are provided. The inelastic strip is placed indirectly or directly onto the nonwoven web, wherein the strips of the nonwoven material are disposed so as to overlap on the edges of the inelastic strip such that the projections extend into the nonwoven material. As previously described, the projections comprise stems and heads on the ends thereof, where the heads have an angling and/or thickening.

The strips of the nonwoven material are installed either before or after the inelastic strip. Therefore, the nonwoven web, the elastically stretchable strips and the strips of nonwoven material can be connected to one another first, wherein a space remains between the elastic strips and wherein the strips of nonwoven material extend there, via the free ends thereof, beyond the elastically stretchable strips. These free ends are then spread apart so that the inelastic strip of hook material or the inelastic strip from which the hook material is formed are placed between the elastically stretchable strips. The spread-apart sections of the nonwoven material are then placed back onto the hook material, wherein a form-fit connection having the projections then results in the overlapping region. If the projections extend through the nonwoven material, the projections can be shaped by pressure and/or temperature in the manner described in order to obtain a form-fit connection in the vertical direction, additionally. At the same time, exposed hooks also can be formed between the edges of the strip of hook material, in the manner described.

When the hook material is initially installed and then the strips of nonwoven material are installed, the strips of the nonwoven material can be placed onto the hook material and the elastically stretchable strips in an overlapping manner, wherein subsequent folding is then no longer necessary.

Another aspect of the invention relates to the formation of a hook material. This hook material Is suitable for the above-described composite web it can be used in other areas. In order to form the hook material, a polymer melt is applied from a slit die into a gap between a roller and a belt, which is guided in sections along the surface of the roller. The roller and/or the belt have a structuring that is provided for forming hooks. Depending on the embodiment of the method, it is possible to form either complete hooks having stems and having heads on the ends or, initially, only the stems of the hooks or the projections, wherein the heads are subsequently produced.

As used herein, hooks should be interpreted to mean elements that are suitable for establishing an interlocking connection in an associated material, for example, in a knitted textile comprising exposed loops, or in a nonwoven material comprising loops. In this case, the hooks can have ends that are bent at the stems or can have mushroom-shaped widenings as the heads.

Since a polymer melt, which is initially still fluid, is dispensed from the slotted nozzle onto the gap, the shaping of the hook of the hook material can be very freely varied. For example, the structuring provided for forming the hooks can be interrupted at sections of the belt or roller such that no hooks are formed there. In particular, the structuring can be interrupted in the transverse direction and/or circumferential direction, wherein hook-free regions are then produced by a flat surface.

In addition to producing regions having hooks or projections and regions that are free of hooks, the described method also can adjust the roller gap and, therefore, the local thickness of the hook material is produced by means of a corresponding contouring of the belt and/or the roller.

When a smooth belt (also referred to as a sleeve) and a structured roller (a chill roll) are used, the stems of the hooks or projections are produced by the structured roller, which is typically cooled (i.e. a chill roll).

Within the scope of the structuring, indentations or cavities for forming the stems of the hooks or projections are formed in the roller. To this end, the roller surface is machined, e.g., using an etching method or by the use of a laser. The number and distribution of the cavities is varied according to the particular application of the hook strip to be formed.

The belt can be produced completely seamlessly, for example, by a galvanic process. Such a belt, which is also referred to as a smoothing belt, depending on the application, is usually tensioned between two temperature-controlled rollers, at least one of which can be driven. The tensioned belt is usually pressed against the structured, cooled roller by a displaceable roller mill. By pressing the belt in a wraparound angle, which usually can be set in a variable manner, it is ensured that the polymer melt, which is initially still fluid, fills the indentations or cavities of the structured roller. As a result, it is possible to eliminate an additional ventilation and therefore a multi-layered design of the roller for ventilation purposes is not required either. By the contact with the circulating belt during the formation of the stems of the hooks or projections, the cooling is better controlled, thereby ensuring that production is carried out even at very high production speeds. The use of the above-described belt also makes it possible to produce a particularly uniform, smooth, and high-quality back side of the hook material.

As explained above, the structuring can be interrupted in the longitudinal direction, the transverse direction, or also in any direction in order to produce hook-free regions.

The hook material also may be formed using a smooth roller and a structured or perforated belt. When a perforated belt is used, it is ensured that the individual holes for producing the stems of the hooks or projections are always sufficiently ventilated. The length of the stems to be formed can be adjusted by the thickness of the belt. As an alternative, the length of the stems can be adjusted by the contact pressure of the belt onto the roller, wherein the holes of the perforation are only partially filled if the contact pressure if reduced. The height of the stems of the hooks is changed by varying the contact pressure, without swapping out the belt.

The hook material can be made of different materials, in a single layer and in multiple layers, depending on the requirement and the application. In a single-layer design, polyolefinic materials such as polyethylene (PE), polypropylene (PP), mixtures of the aforementioned polymers, and a copolymer of polyethylene and polypropylene are suitable. Preferably, stiff types of PP are used, present as homopolymers or as copolymers. In addition, other polymers also are suitable for a single-layered or multi-layered design. Relatively stiff materials such as cyclic olefin copolymer (COC) polyesters such as, e.g., polyethylene terephthalate (PET), polyamides (PA) such as PA 6 and PA 6.6, or polymethyl methacrylate (PMMA), also are advantageous, in particular.

In a multi-layered design of the hook strip, the requirements on, e.g., stiffness, flowability during production, and compatibility with the adjacent layers in the laminate (some of which oppose one another) is advantageously fulfilled. Advantageously, embodiments that comprise largely one material or at least embodiments made entirely of polyolefin are possible, whereby recycling is simplified. In the case of a three-layered design, for example, polypropylene (PP) may be provided for all layers, wherein, the layer from which the hooks or projections are intended to be made is selected with regard for an improved embossing behavior having a high flow index (MFI). As such, the remaining layers are specifically optimized with regard for the required stiffness of the hook strip.

In addition to such a single-material design, a multi-layered design comprising different material types is also possible, wherein the outer layers preferably comprise materials based on a polyolefin (e.g., PP). In a design comprising at least three layers, an inner core layer is selected with regard for maximum stiffness. Whereas a primer layer is disposed between the core layer and the outer layers in a five-layered design, in the case of a three-layered design, a sufficient connection of the layers with one another can be achieved by means of functionalized or modified polyolefins.

The thickness of the hook material underneath the hooks or projections is typically between 20 and 180 μm, particularly preferably between 70 and 140 μm.

BRIEF DESCRIPTION OF THE DRAWINGS

Further features and advantages of the invention will become apparent from the description of embodiments that follows, with reference to the attached figures, wherein.

DETAILED DESCRIPTION OF THE PREFERRED EMBODIMENTS

The following is a detailed description of example embodiments of the invention depicted in the accompanying drawings. The example embodiments are presented in such detail as to clearly communicate the invention and are designed to make such embodiments obvious to a person of ordinary skill in the art. However, the amount of detail offered is not intended to limit the anticipated variations of embodiments; on the contrary, the Intention is to cover all modifications, equivalents, and alternatives falling within the spirit and scope of the present invention, as defined by the appended claims.

Figure 1:
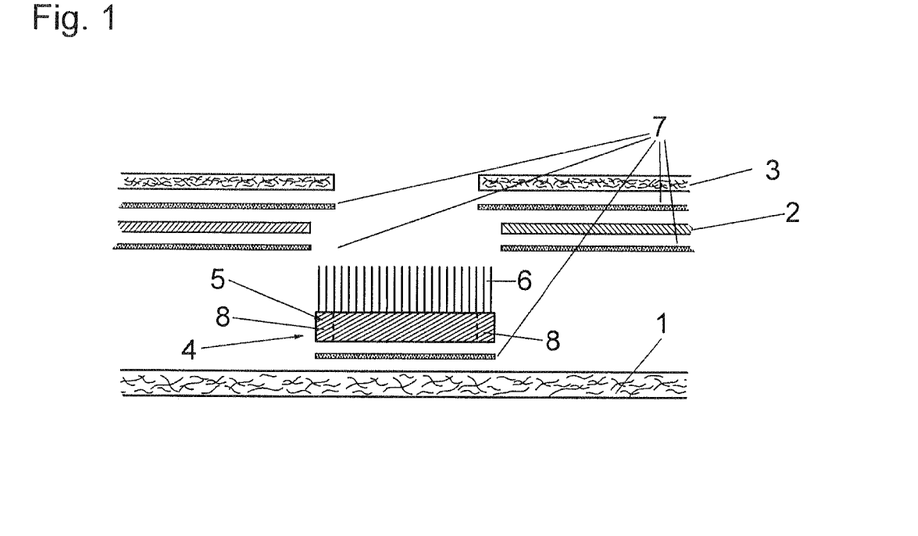
FIG. 1 depicts the components from which a composite web, according to the inventive principles.

FIG. 1 shows a cross-section of the individual components from which a composite web having elastic and inelastic regions is formed, from which diaper closure elements can be punched or separated.

The composite web comprises a flat nonwoven web 1, which forms a first outer side of the composite web. In order to produce the elastic regions of the composite web, elastically stretchable foil strips 2, which are spaced apart from one another in parallel, are disposed on the nonwoven web 1, wherein these foil strips 2 are covered by a nonwoven material 3. The nonwoven material 3, which is disposed in the form of nonwoven strips, completely covers the foil strips 2 and, in regions, forms a second outer side of the composite web. In addition, an inelastic strip 4 is provided, from which a hook material is formed. The inelastic strip 4 comprises a carrier section 5 and upwardly protruding stems 6.

The described components can be connected to one another in different manners. In particular, bonding all-over or in sections is implemented using adhesive 7 or ultrasonic welding. When the bonding is provided only in sections, the connection is expediently established by adhesive strips, which extend along the longitudinal direction of the above-described, strip-shaped elements.

FIG. 1 shows the individual components of the composite web, wherein a planar application of adhesive 7 is shown merely as an example.

It is evident in FIG. 1 that the two elastically stretchable foil strips 2 are disposed laterally relative to the inelastic strip 4, while the nonwoven material 3 overlaps edges 8 of the inelastic strip 4.

Figure 2:
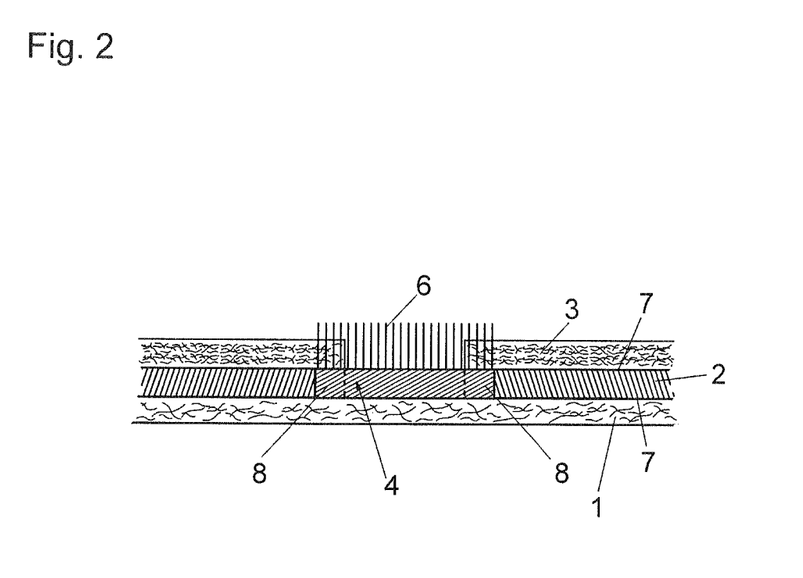
FIG. 2 depicts the components connected to one another.

When the inelastic strip 4 is first disposed on the nonwoven strip 1 before the elastically stretchable foil strips 2 and the strips of nonwoven material 3 are supplied, the nonwoven material 3 at the overlapping edges 8 is punctured by the stems 6 at the edges 8 as soon as said nonwoven material is supplied, whereby the nonwoven material 3 is held by the stems 6 (FIG. 2).

The stems 6 are then projections 9 at the edges 8, which extend into the nonwoven material 3 and through the nonwoven material 3.

Figure 3:
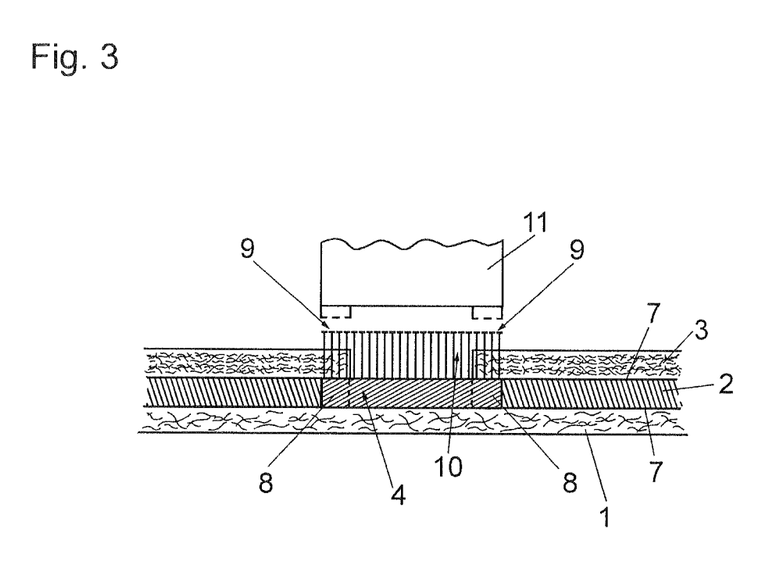
FIG. 3 depicts a method step for producing hooks, according to the inventive principles.

In order to form exposed hooks 10 between the overlapped edges 8, the stems 6 are shaped under the effect of pressure and temperature by means of a suitable tool 11 (FIG. 3), wherein heads having an angling and/or thickening are produced. The stems 6 at the overlapped edges 8 also are shaped in the same manner, wherein the nonwoven material 3 is fixed, in a form-fit connection, not only in the plane of the composite web, but also perpendicularly thereto. Within the scope of the invention, a tool 11 also can be used, which more extremely shapes the stems 6 forming the projections 9 than the stems 6 from which the exposed hooks 10 are formed.

Figure 4:
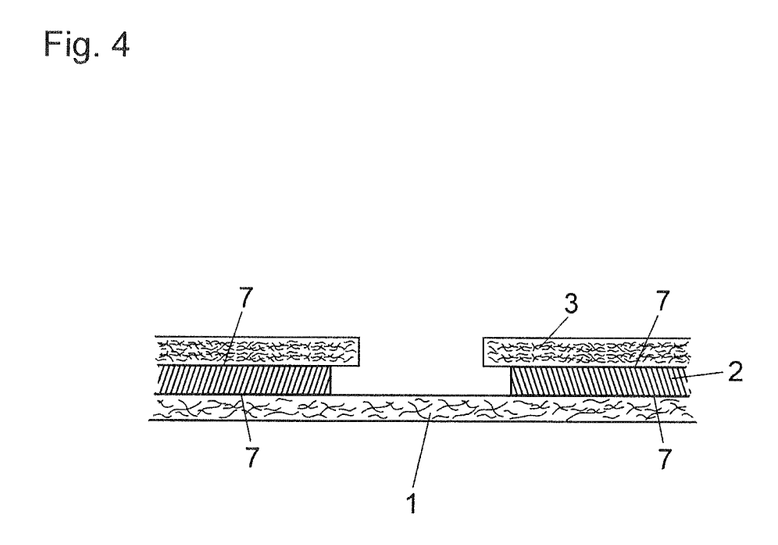
FIG. 4 depicts a variant of the method for producing the composite web.
Figure 5:
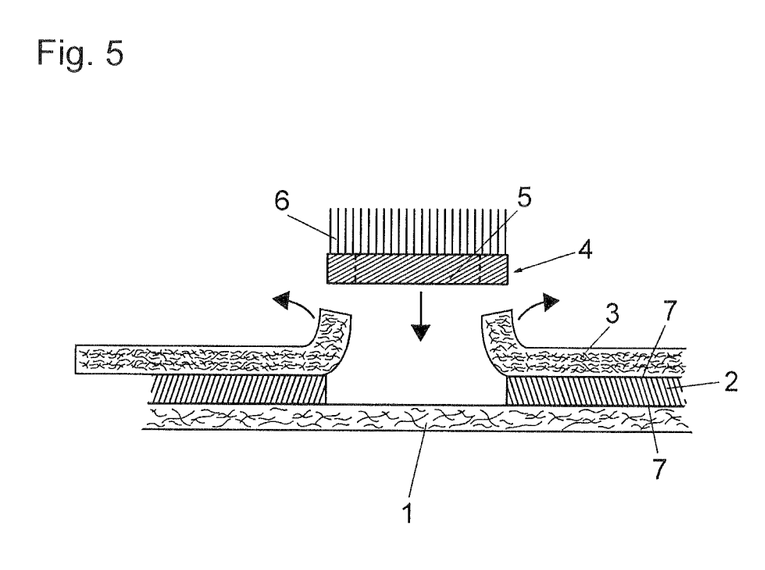
FIG. 5 depicts a variant of the method for producing the composite web.
Figure 6:
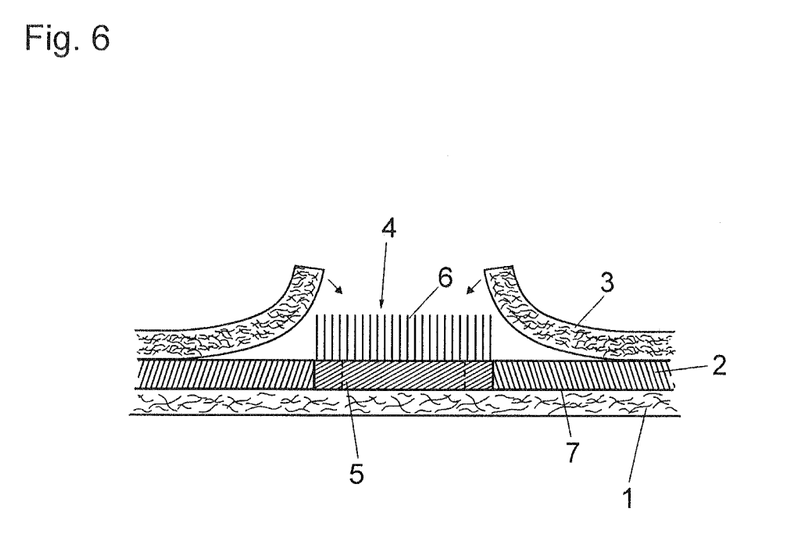
FIG. 6 depicts a variant of the method for producing the composite web.

FIG. 4. to 6 show an alternative procedure for producing the composite web, wherein the nonwoven web 1, the elastic foil strips 2, and the strips of the nonwoven material 3 are first connected to one another, e.g., by means of adhesive 7 (FIG. 4). As is also shown in FIG. 1, the strips of the nonwoven material 3 extend beyond the foil strips 2. The inelastic strip 4 is then inserted by folding back the exposed lateral ends of 10' the nonwoven material 3 (FIG. 5):

After the nonwoven material is folded back (FIG. 6), the arrangement according to FIG. 2 results, wherein the stems 6 also are subsequently shaped in this case.

Figure 7:
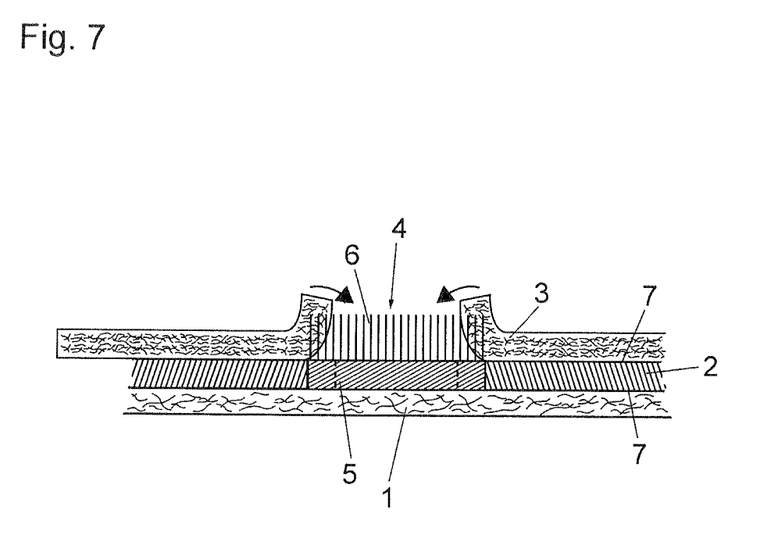
FIG. 7 depicts an alternative embodiment of the composite web, according to the inventive principles.

FIG. 7 shows an embodiment, wherein the stems 6 have a shorter length at the overlapped edges 8. The projections 9 formed by the stems 6 at the overlapping edges 8 then extend only into the nonwoven material 3, but not entirely through the nonwoven material 3. Nevertheless, a reliable fixation is achieved at least in the plane of the composite web, wherein the nonwoven material 3 can also be bonded on the carrier section 5 of the inelastic strip 4.

Figure 8:
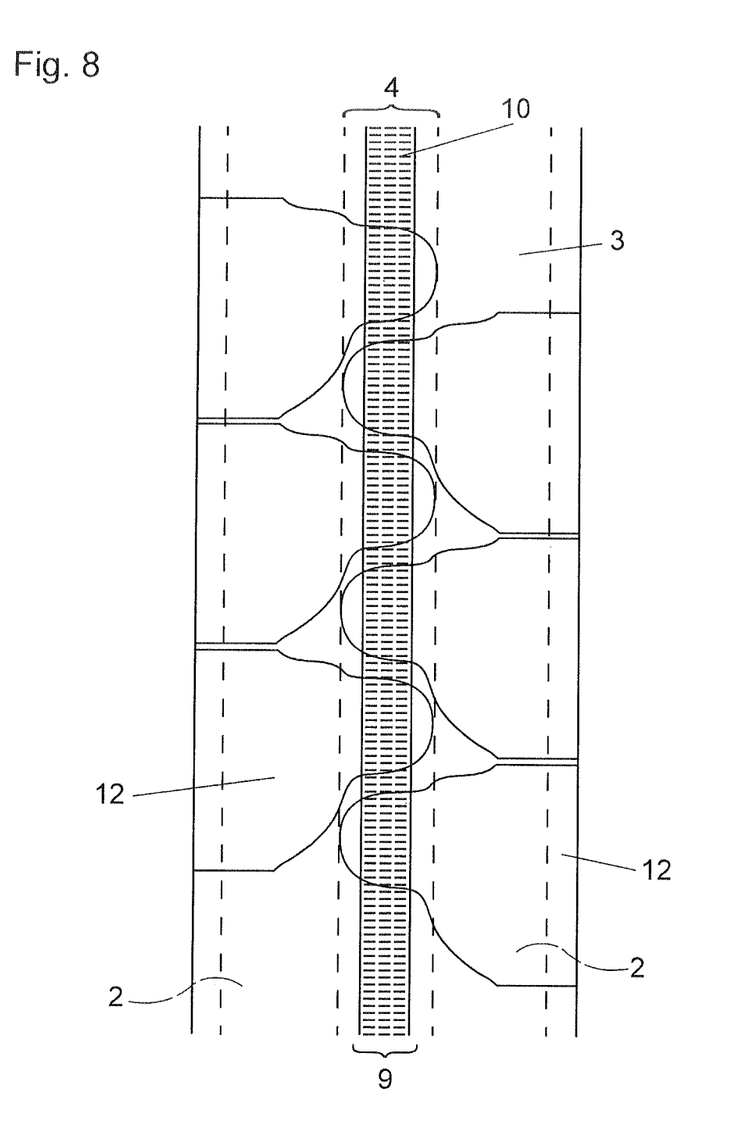
FIG. 8 depicts a top view of a composite web having a pattern for separating individual closure elements, according to the inventive principles.

FIG. 8 shows one possible cutting or punching pattern for producing individual closure elements 12. As shown In FIG. 8, the region of the inelastic strip 4 provided with hooks 10 extends along the entire width of each closure element 12. In addition, a free end of the closure element 12 is formed next to the hooks 10 by a section of the composite web that comprises the projections 9. In particular, when the projections 9 extend through the nonwoven material 3, a more pronounced shaping is provided there by the tool 11 during production in order to produce the most uniform, smooth gripping section possible for a user.

Figure 9:
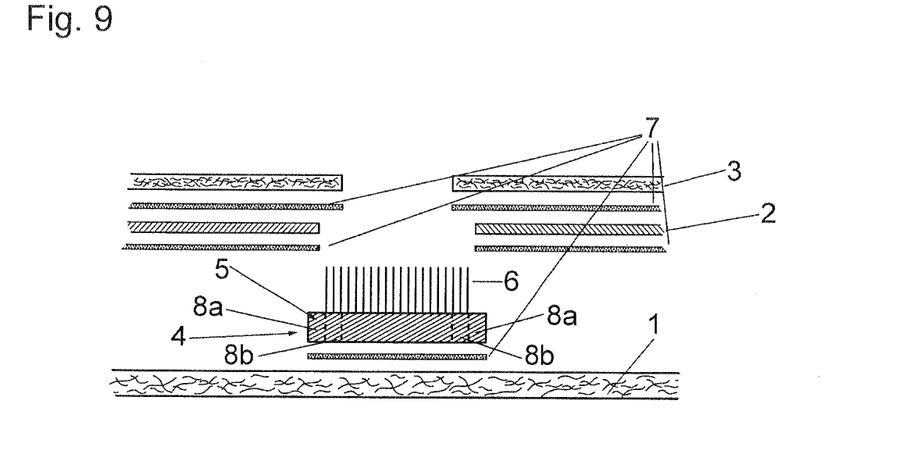
FIG. 9 depicts an alternative embodiment of the composite web, according to the inventive principles.

FIG. 9, which proceeds from FIG. 1, shows an embodiment of the composite web, in which a first outer edge section 8a, which is covered by the nonwoven material 3, is free of hooks 10 and stems 6. Whereas the elastically stretchable foil strips 2 terminate at the outer edge section 8a, the nonwoven material 3 extends therebeyond to a second, further inwardly located edge section 8b, which comprises upwardly protruding stems 6.

As will be evident to persons skilled in the art, the foregoing detailed description and figures are presented as examples of the invention, and that variations are contemplated that do not depart from the fair scope of the teachings and descriptions set forth in this disclosure. The foregoing is not intended to limit what has been invented, except to the extent that the following claims so limit that.

What is claimed is:

1. A composite web with elastic and inelastic regions, the composite web configured to be separated or punched into diaper closure elements and comprising:
   a nonwoven web that forms a first outer side of the composite web;
   elastically stretchable strips spaced apart from one another and disposed on the nonwoven web;
   a nonwoven material that covers the elastically stretchable strips on a second outer side of the composite web; and
   at least one inelastic strip of hook material that bridges a region between two adjacent, elastically stretchable strips;
   wherein the nonwoven material overlaps edges of the at least one elastic strip of hook material;
   wherein the strip of hook material has projections on the edges thereof that are overlapped by the nonwoven material and extend into the nonwoven material.

2. The composite web according to claim 1, wherein the projections extend through the nonwoven material.

3. The composite web according to claim 2, wherein the projections comprise heads on the ends thereof, the heads having an angling, a thickening or both.

4. The composite web according to claim 3, wherein the projections are disposed on a carrier section of the hook material and wherein the nonwoven material rests on the carrier section at the overlapped edges.

5. The composite web according to claim 1, wherein the strip of hook material has exposed hooks between the edges that are covered by the nonwoven material and wherein the exposed hooks and the projections have the same shape.

6. A method for the producing a composite web for separation of punching into diaper closure elements, the method comprising the steps of:
   disposing elastically stretchable strips spaced apart from one another on a nonwoven web, which nonwoven web forms an outer side of the composite web;
   disposing an inelastic strip of hook material that bridges a region between two adjacent, elastically stretchable strips, on the nonwoven web; and
   covering the elastically stretchable strips with strips of a nonwoven material to form a second outer side of the composite web; and
   wherein the strips of the nonwoven material overlap edges of the inelastic strip of hook material; and
   wherein the inelastic strip of hook material has projections on the edges thereof that are overlapped by the strips of the nonwoven material and that extend into the nonwoven material.

7. The method according to claim 6, wherein the projections provided on the inelastic strip are in a form of stems and wherein the strips of the nonwoven material are disposed so as to overlap on the edges of the inelastic strip such that the stems extend through the nonwoven material.

8. The method according to claim 7, wherein the stems at the edges of the inelastic strip are angled or are provided with a thickening at the ends thereof after the strips of the nonwoven material are placed so as to overlap.

9. The method according to claim 8, further comprising shaping the stems by pressure, by temperature or both.

10. The method according to claim 8, wherein stems are disposed between the edges of the inelastic strip and wherein the stems are shaped to form exposed hooks.

* * * * *